(12) United States Patent
Hu (10) Patent No.: US 9,475,759 B2
(45) Date of Patent: Oct. 25, 2016

(54) TIGECYCLINE CRYSTALLINE HYDRATE AND PREPARATION METHOD THEREFOR AND USE THEREOF

(76) Inventor: Lifang Hu, Foshan (CN)

( * ) Notice: Subject to any disclaimer, the term of this patent is extended or adjusted under 35 U.S.C. 154(b) by 219 days.

(21) Appl. No.: 14/112,876

(22) PCT Filed: Apr. 20, 2012

(86) PCT No.: PCT/CN2012/074409
§ 371 (c)(1),
(2), (4) Date: Jan. 3, 2014

(87) PCT Pub. No.: WO2012/142958
PCT Pub. Date: Oct. 26, 2012

(65) Prior Publication Data
US 2014/0107357 A1    Apr. 17, 2014

(30) Foreign Application Priority Data
Apr. 20, 2011 (CN) .......................... 2011 1 0099884

(51) Int. Cl.
C07C 237/26 (2006.01)
A61K 31/65 (2006.01)
C07C 231/14 (2006.01)

(52) U.S. Cl.
CPC ............ *C07C 237/26* (2013.01); *A61K 31/65* (2013.01); *C07C 231/14* (2013.01); *C07B 2200/13* (2013.01); *C07C 2103/46* (2013.01)

(58) Field of Classification Search
CPC .... C07C 237/26; C07C 231/14; A61K 31/65
See application file for complete search history.

(56) References Cited

U.S. PATENT DOCUMENTS

| 2007/0049562 | A1 | 3/2007 | Krishnan et al. |
| 2007/0123497 | A1 | 5/2007 | Krishnan et al. |
| 2009/0005453 | A1* | 1/2009 | Tsiperman ............ C07C 237/26 514/616 |
| 2010/0152142 | A1 | 6/2010 | Levi et al. |

FOREIGN PATENT DOCUMENTS

CN    101228112 A    7/2008

OTHER PUBLICATIONS

Price, Chemical Society Reviews, Predicting Crystal Structures of Organic Compounds, 2014, 43, pp. 2098-2211.*
Braga et al, Structure and Bonding, Crystal Polymorphism and Multiple Crystal Forms, 2009,132, pp. 25-50.*
International Search Report mailed Jun. 21, 2012 (PCT/CN2012/074409); ISA/CN.

* cited by examiner

*Primary Examiner* — Paul A Zucker
(74) *Attorney, Agent, or Firm* — Banner & Witcoff, Ltd.

(57) ABSTRACT

Provided are a Tigecycline crystalline hydrate, and a preparation method therefor and use thereof. The crystalline hydrate has high stability for storage, and is used for the manufacture of a medicament for treating or preventing the infection of respiratory system, hepatobiliary system, facial features, urogenital system, bone and joint, skin and soft tissue and endocarditis, septicemia, meningitis caused by susceptible strains of Gram-positive or Gram-negative bacteria, anaerobic bacteria, chlamydia, and mycoplasma in human or animal.

13 Claims, 5 Drawing Sheets

TIGECYCLINE CRYSTALLINE HYDRATE AND PREPARATION METHOD THEREFOR AND USE THEREOF

TECHNICAL FIELD

The invention relates to the field of medicinal technology, particularly, to provide antibacterial medicines, tigecycline crystalline hydrates, and preparation method therefor and use thereof.

BACKGROUND

Currently, published documents only report that tigecycline ($C_{29}H_{39}N_5O_8$, molecular weight: 585.65, Cas No: 220620-09-7) or amorphous tigecycline. The tigecycline is a well known tetracycline antibiotic, and it is an analogue of the minocycline. The tigecycline has broad-spectrum antibacterial activities both in vitro and in vivo, and it is used against drug-resistant bacteria. Furthermore, it has been found that the tigecycline is still effective to some diseases which other antibiotics fails to treat (reference document 1, Sader H S, Farrell D J, Jones R N. Tigecycline activity tested against multidrug-resistant Enterobacteriaceae and *Acinetobacter* spp. isolated in US medical centers (2005-2009). Diagn Microbiol Infect Dis. 2011, 69(2): 223-7; reference document 2, George A. Pankey, Tigecycline, Journal of Antimicrobial Chemotherapy (2005) 56, 470-480). The tigecycline provides physicians a novel broad-spectrum antibiotic which can be selected at incipient stage of pathogenesy when disease causes are still not be recognized. Furthermore, it is not required to adjust the dose of the antibiotic according to situations of impaired renal functions, and it has the advantages of convenient uses, i.e., in general, one administration every 12 hour.

So far, there are still not public literatures at home and abroad to report tigecycline crystalline hydrates and preparation method therefor and use thereof.

SUMMARY OF THE INVENTION

The invention relates to an antibacterial of tigecycline crystalline hydrates, and preparation method therefor and use thereof, and further, to the antibacterial, i.e., pharmaceutically acceptable crystalline hydrates of the tigecycline, and to preparation method therefor and use thereof. The tigecycline crystalline hydrates have a molecular formula of $C_{29}H_{39}N_5O_8 \cdot nH_2O$, n is a number between 0.4 and 2, including 0.5, 1.5, 2, 4, etc.

Tigecycline containing crystalline water obtained in the invention, surprisingly, has a far low hygroscopicity than tigecycline anhydrides. The tigecycline containing crystalline water can exist more stably than tigecycline anhydrides, and it is easy to be stored and transported and ready to be formulated. In addition, due to the moisture-decomposition of an anhydride, the anhydride should be isolated from air during treatments to prevent adhesion. Crystalline hydrates have a good sliding property, so that the operability of formulations can be improved. Furthermore, a crystalline solid has higher chemical stability and physical stability than its amorphous form and low-crystallization-level form, and it can exhibit an improved moisture absorption, bulk performance and/or fluidity.

Discoveries to new pharmaceutically useful polymorph compounds provide a new opportunity to improve action characteristics of a medicinal product, and for the formulation scientists they expand the library of materials obtained, for example, by designing a formulation containing a medicine having a target release profile or other desirable characteristics. Hence, the tigecycline or its polymorphs are in need in the art.

Surprisingly and characteristically, the thermogram (TG-DSC or TG-DTA) of the hydrates according to the invention has corresponding endothermic peaks at a weightless platform. The thermogram shows tigecycline crystalline hydrate, tigecycline.$0.5H_2O$ hydrate, etc. The product is a red to orange-yellow crystalline powder; when the crystalline product is in a system selected from water and acetone, diethyl ether, and ethanol, it is a red to orange-yellow crystalline hydrate, the color being better than its anhydride. This facilitates the reduction of side effects in clinical, thereby to increase the safety of the medicine.

The tigecycline crystalline hydrates according to the invention can be stable for storage. A hygroscopicity test is conducted directed to a tigecycline hydrate sample and a tigecycline anhydride sample: about 5 g of the tigecycline anhydride and 5 g of the hydrate of the invention are taken, and they are placed in a dry and weight-constant surface vessel and precisely weighted. At 25° C. and in a relative humidity of 70%, the percentage of hydroscoical weight gain is calculated by respectively sampling at 0 h and 16 h. Results show that the hydroscopicity of the anhydride is far higher than that of the hydrate of the present invention, and the results regarding that the tigecycline crystalline hydrate of the invention may be more stable for storage are shown in Table 1. On the conditions of RH 75% and 30° C., the tigecycline crystalline hydrate is sealed in a vial for conducting a six-month acceleration stability test. According to the testing conditions of HPLC process of the tigecycline in relevant literatures: $C_{18}$ (250 mm×4.6 mm, 5 μm) acetonitrile:phosphate buffer (1.29 g of citric acid and 2.76 g of anhydrous disodium hydrogen phosphate are dissolved in water and diluted to 1000 ml) (80:20) as the mobile phase; detection wavelength is 248 nm; the column temperature is room temperature; and the flowing rate is 1 ml/min. Under the conditions, the tigecycline contents and related substances are determined.

Results show that the contents are constant, the related substances do not significantly increase, and the amplitude of the increase of epimerides is significantly lower than that of controls. The experimental results show that the tigecycline crystalline hydrate of the invention has excellent storage stability.

The preparation for tigecycline derivatives, i.e., tigecycline crystalline hydrates, comprises the following methods:

Method A:
1) The Preparation of 9-Nitrominocycline

Minocycline hydrochloride (1) was dissolved in a concentrated sulfuric acid which is pre-cooled to 0° C., and then at the temperature of from −5 to 5° C., a potassium nitrate or fuming nitric acid is slowly added thereto. After the addition, the mixture is stirred continuously at −5 to 5° C. for 1.5 h. A pre-cooled $C_5$-$C_{10}$ linear or branched alkane or cycloalkane is slowly added, then filtered, and after the reaction mixture is washed with an icy $C_5$-$C_{10}$ linear or branched alkane or cycloalkane, solids are collected and dried under vacuum at the temperature of 40 to 50° C. to give yellow 9-nitrominocycline disulfate (2).

Therein, the weight-volume ratios of the reactants used in the reaction are generally as follows: minocycline hydrochloride (g):concentrated sulfuric acid (ml):potassium nitrate or fuming nitric acid (g):$C_5$-$C_{10}$ linear or branched alkane or cycloalkane (ml)=100:300-330:20-25 or (11-13 ml):1500-3000.

2) The Preparation of 9-Aminominocycline 9-nitrominocycline disulfate (2) is placed to a mixture of 2% palladium on carbon and 2N sulfuric acid solution with ethylene glycol monoethyl ether. The mixture is hydrogenated on a raised pressure for about 1.5 h, or on normal pressure for about 4 h. The catalyst is filtered, and the obtained filtrate is slowly added to low-molecular $C_1$-$C_6$ alcohols or linear or branched $C_5$-$C_{10}$ alkane or cycloalkane at 0 to 5° C. The obtained solution is filtered to give a slightly yellow crystal. The crystal is dried under vacuum at 40° C. to give 9-aminominocycline disulfate (3).

Therein, the weight-volume ratios of the reactants used in the reaction are generally as follows: 9-nitrominocycline disulfate (g):2N sulfuric acid (ml):2% palladium on carbon (g):ethylene glycol monoethyl ether (ml):low-molecular $C_1$-$C_6$ alcohols or linear or branched $C_5$-$C_{10}$ alkane or cycloalkane (ml)=100:200-350:300-500:2000-4000.

3) The Preparation of Tigecycline Crystalline Hydrates

Direct Acylation of 9-Aminominocycline with N-Tert-Butyl Acetyl Chloride or N-Tert-Butyl Acetic Acid 9-amino minocycline disulfate, and sodium hydrogen carbonate or sodium carbonate or potassium carbonate, are suspended in a mixed solvent of 1,3-dimethyl propylidene urea/a lower $C_2$-$C_6$ nitrile, and a solution of N-tertbutyl acetyl chloride and 1,3-dimethyl propylidene urea/a lower $C_2$-$C_6$ nitrile is added dropwise at room temperature with stirring. After the addition, the mixture is stirred continuously for 30 min. After the reaction is completed, a low-molecular $C_1$-$C_6$ alcohol is added to terminate the reaction. The obtained reaction liquor is poured into one or more solutions selected from low-molecular $C_1$-$C_6$ alcohols, lower $C_2$-$C_6$ nitriles, or lower $C_2$-$C_8$ ethers, and a concentrated hydrochloric acid is added thereto to precipitate crystals, which are filtered to give yellow crystals, i.e., tigecycline hydrochloride (5.HCl). The tigecycline hydrochloride is dissolved in deionic water, and 10% aqueous ammonia is added thereto to adjust the pH to about 7.0, so that crystals are precipitated and filtered. The obtained solid is recrystallized one or several times with water and one or more selected from low substituted halogenated $C_1$-$C_6$ hydrocarbons, lower $C_3$-$C_8$ ketones, low-molecular $C_1$-$C_6$ alcohols, lower $C_2$-$C_6$ nitriles, lower $C_2$-$C_8$ esters, lower $C_2$-$C_8$ ethers or $C_6$-$C_{12}$ aromatic hydrocarbons, and the obtained crystals are dried under vacuum to give the tigecycline crystalline hydrate.

Therein, the weight-volume ratios of the reactants used in the reaction are generally as follows: 9-aminominocycline disulfate (g):sodium bicarbonate or sodium carbonate or potassium carbonate (g):1,3-dimethyl propylidene urea and a lower $C_2$-$C_6$ nitrile (ml):N-tert-butyl acetyl chloride (g): 1,3-dimethyl propylidene urea and a lower $C_2$-$C_6$ nitrile (ml, the solvent for N-tert butyl acetyl chloride):a low-molecular $C_1$-$C_6$ alcohols (ml):a low-molecular $C_1$-$C_6$ alcohols, a lower $C_2$-$C_6$ nitrile or a lower $C_2$-$C_8$ ether (ml)=20:15~:40: 200-300:9-10:200-800:10-30:200-1000.

Method B

1) The Preparation of 9-Haloacetylamino Minocycline 9-nitrominocycline disulfate (20 g, 0.03 mol) is suspended with 1,3-dimethyl propylidene urea (400 ml) and acetonitrile (100 ml), and sodium carbonate (20 g) was added thereto at room temperature, stirred for 30 min. Then, bromoacetyl bromide (12.2 g, 0.06 mol) or chloroacetyl chloride (6.68 g, 0.06 mol) are slowly added dropwise, and after the addition, the mixture is stirred continuously for 1 h, filtered to remove solids. The obtained filtrate is slowly poured into one or more solvents in 20 to 60 times [the ratio is the weight-volume ratio of 9-nitrominocycline disulfate to the solvent (g:ml)] selected from lower $C_3$-$C_8$ ketones, low-molecular $C_1$-$C_6$ alcohols, lower $C_2$-$C_6$ nitriles, lower $C_2$-$C_8$ esters, and lower $C_2$-$C_8$ ethers, filtered to collect yellow precipitation. The precipitation is washed with a small amount of one or more solvents selected from lower $C_3$-$C_8$ ketones, low-molecular $C_1$-$C_6$ alcohols, lower $C_2$-$C_6$ nitriles, lower $C_2$-$C_8$ esters, lower $C_2$-$C_8$ ethers, and the obtained 9-bromoacetylamino minocycline bromide (4a) or 9-chloroacetylamino minocycline chloride (4b) is dried under vacuum, at 40° C.

Therein, the weight-volume ratios of the reactants used in the reaction are generally as follows: 9-amino minocycline disulfate (g):1,3-dimethyl propylidene urea and a lower $C_2$-$C_6$ nitrile (ml):sodium bicarbonate or sodium carbonate or potash (g):bromoacetyl bromide or chloroacetyl chloride: low-molecular $C_1$-$C_6$ alcohols (ml):low-molecular $C_1$-$C_6$ alcohols, lower $C_2$-$C_6$ nitriles or lower $C_2$-$C_8$ ethers (ml) =20:200-300:15~:40:6.7-13:400-1200.

2) The Preparation of Tigecycline Crystalline Hydrates

The amination of 9-haloacetylamino minocycline with tert-butylamines 9-bromoacetylamino minocycline hydrobromide or 9-chloroacetylamino minocycline hydrochloride is mixed with tert-butyl amine and a low-molecular $C_1$-$C_6$ alcohol, and the mixture is stirred at room temperature for 20-60 min, filtered to remove precipitation. The filtrate is concentrated under reduced pressure, and the residual is recrystallized one or several times with water and one or more of low substituted halogenated $C_1$-$C_6$ hydrocarbons, lower $C_3$-$C_8$ ketones, low-molecular $C_1$-$C_6$ alcohols, lower $C_2$-$C_6$ nitrile, lower $C_2$-$C_8$ esters, lower $C_2$-$C_8$ ethers or $C_6$-$C_{12}$ aromatic hydrocarbons, filtered to give a tigecycline crystalline hydrate.

Therein, the weight-volume ratios of the reactants used in the reaction generally are as follows: 9-bromoacetylamino minocycline hydrobromide or 9-chloroacetylamino minocycline hydrochloride (g):tert-butylamine (ml):a low-molecular $C_1$-$C_6$ alcohol (ml)=10-15:10-20:100-200.

Solvents for crystallization or recrystallization of tigecycline crystalline hydrates are selected from water and organic solvents selected from the group consisting of lower $C_3$-$C_8$ ketones, lower $C_2$-$C_6$ nitriles, low-molecular $C_1$-$C_6$ alcohols, lower $C_2$-$C_8$ ethers, lower $C_2$-$C_8$ esters, low substituted halogenated $C_1$-$C_6$ hydrocarbons or $C_6$-$C_{12}$ aromatic hydrocarbons. The solvents for crystallization or recrystallization of the tigecycline crystalline are preferably water and one or more solvents selected acetonitrile, tetrahydrofuran, methanol, ethanol, isopropanol, ethyl acetate, dichloromethane, chloroform, diethyl ether, diisopropyl ether or benzene. The volume ratio of water to an organic solvent used in the crystallization or recrystallization of the invention is generally 1:5-200, relatively preferably 1:50-100, and more preferably 1:50-98.

The carbon atom number of a lower alcohol or a low-molecular-weight alcohol of the present invention is defined to be $C_1$-$C_6$ (i.e.: an alcohol of 1-6 carbon atoms), such as methanol, ethanol, isopropanol, butanol and the like; the carbon atom number of a lower $C_2$-$C_6$ nitrile is defined to be $C_2$-$C_6$, such as acetonitrile, propionitrile, and the like; the carbon atom number of a lower $C_2$-$C_8$ ether or low-molecular ether is defined to be $C_2$-$C_8$, such as diethyl ether, diisopropyl ether, dibutyl ether, and the like; the carbon atom number of a lower halogenated hydrocarbon is defined to be $C_1$-$C_6$ (i.e. from 1 to 6 carbon atoms), including dichloromethane, dichloroethane, chloroform, and the like; the carbon atom number of a lower ester is defined to be $C_2$-$C_8$ (i.e. 2-8 carbon atoms), including butyl acetate, ethyl acetate, ethyl formate, and the like; the carbon atom number of a low-molecular straight or branched alkane or cycloalkane is defined to be $C_5$-$C_{10}$ (i.e. 5-10 carbon atoms), including pentane, hexane, cyclohexane, petroleum ether, and the like; the carbon atom number of a low-molecular aromatic hydrocarbon is defined to be $C_6$-$C_{12}$ (i.e. 6-12 carbon atoms), including benzene, toluene, and the like; the carbon atom number of a low-molecular $C_3$-$C_8$ ketone is defined to be a ketone having 3 to 8 carbon atoms, including acetone, butanone, isohexyl ketone, and the like. Only if a method for marking the carbon atom number of any as described "lower or low-molecular" compound is involved once in the text, the carbon atom numbers of other compounds of the same class which are not marked but described as "lower or low-molecular" compounds are consistent with the carbon atom numbers of compounds which have marked herein.

Methods for drying the product of the present invention are as follows: drying is conducted to the final product under the environmental conditions of different temperatures (such as 20-60° C.), drying time (1 hour to several days), or with other desiccants (including silica gel, phosphorus pentaoxide, anhydrous calcium chloride, anhydrous sodium sulfate, etc.), or under atmospheric pressure or reduced pressure. The drying temperature is preferably at 25-45° C.

In another aspect, the present invention provides a pharmaceutical composition comprising any one or more tigecycline crystalline hydrates prepared by the method of the present invention, and one or more pharmaceutically acceptable excipients.

The present invention further provides a method of preparing a pharmaceutical formulation including combinations of any one or more tigecycline crystalline hydrates and at least one pharmaceutically acceptable excipient.

The invention further provides use of tigecycline crystalline hydrates, such as tigecycline.0.5$H_2O$ hydrate, tigecycline.2$H_2O$ hydrate, tigecycline.4$H_2O$ hydrate and the like, in the manufacture of a medicament for treating infections, including bacterial infections, Gram-positive and Gram-negative bacterial infections, and the lethal infections.

The tigecycline crystalline hydrates of the present invention are used to prepare compositions comprising the tigecycline crystalline hydrates. The compositions comprise solid preparations, suppositories, injections of the tigecycline crystalline hydrates, in which the injections include freeze-dried powder formulation for injection. The tigecycline crystalline hydrates of the present invention also can be used to prepare tigecycline anhydrides. Anhydrides can be prepared from the crystalline hydrates of the present invention by different drying methods, and the preparation can be conducted under environmental conditions of different temperature (such as 50-100° C.), drying time (1 hour to 48 hours), or with other desiccants (including silica gel, molecular sieve, phosphorus pentaoxide, sodium hydroxide, anhydrous sodium carbonate, anhydrous calcium chloride, anhydrous sodium sulfate, anhydrous magnesium sulfate, etc.), or under atmospheric pressure or reduced pressure. The anhydrides also may be prepared by benzene distillation and combining other drying methods as described herein.

Examples of solid formulations of tigecycline crystalline hydrates include tablets, capsules, granules and the like; the tablets (including buccal tablets, rapidly disintegrating tablets, effervescent tablets, soluble tablets, vaginal tablets, etc.), capsules (including vaginal capsules), and granules may comprise pharmaceutically acceptable fillers, such as starch, modified starch, lactose, microcrystalline cellulose, cyclodextrin, sorbitol, mannitol, calcium phosphate, amino acids, etc.; pharmaceutically acceptable disintegrants, such as starch, modified starch, microcrystalline cellulose, sodium carboxymethyl starch, crosslinked polyvinylpyrrolidone, low-substituted hydroxypropyl cellulose, surfactants (sodium dodecyl sulfate); pharmaceutically acceptable wetting agents and binders, such as gelatinized starch, methyl cellulose, sodium carboxymethyl cellulose, ethyl cellulose, polyvinylpyrrolidone, alginic acid and salts thereof; pharmaceutically acceptable lubricants and glidants, such as stearic acid, magnesium stearate, polyethylene glycol 4000-8000, talc, aerosil, magnesium lauryl sulfate, etc.; pharmaceutical acceptable sweeteners and flavors, such as aspartame, sodium cyclamate, sodium saccharin, sucralose, edible essence, etc.

Compositions useful for the preparation of tablets or capsule filler may be prepared by wet granulation. During the wet granulation, some or all active ingredients are mixed with excipients in powder form, and then they are further mixed in the presence of liquids, thereby resulting in the clot of powder into granules. The granules are sieved and/or grinded, dried, and then sieved to get granules having desirable particle sizes. Then, the granules may be prepared into tablets, or prior to the preparation, other excipients, such as glidants and/or lubricants, are added thereto.

Compositions which are prepared into tablets generally may be prepared by dry mixing. For example, a composition obtainable by mixing active ingredients and excipients can be compressed into small pieces or flakes, and then comminuted into compacted granules. Subsequently, the compacted granules can be compressed into tablets.

As an alternative to dry granulation, the mixed composition may be directly tableted by drying methods. Direct tableting can produce more uniform tablets. The excipients particularly suitable for direct tableting include microcrystalline cellulose, spray-dried calcium lactose phosphate and colloidal silica. Correct uses of these excipients and other excipients in direct tableting are well known for experienced and skilled technical persons in the art Filling materials for capsules of the present invention can include any of the above mixtures and granules or particles, and as to descriptions for their preparations, please see the preparation of tablets, except that the step of final tableting is not conducted.

The crystalline hydrates of the invention are different from anhydrides which is required to be isolated from air during treatments due to moisture-decomposition to prevent adhesions. However, a crystalline hydrate has good sliding properties, thereby improving the operability of the preparation, and it can make prepared solid preparations have good dissolution such that the compound is easily absorbed into the blood circulation, thereby to improve bioavailability, and to facilitate rapidly acting its functions. On the other hand, the use of the crystalline hydrate may prevent the following disadvantages: insufficient doses are caused by different loadings which will be produced during sterile separation package for the reasons of moisture absorption which will result in clotting during package, thereby producing unqualified products; or unqualified products are not checked, thereby resulting in actual missed sampling, so that the unqualified products enter markets to produce negative effects on the treatments to a patient, or endanger patient's life due to insufficient doses; or upon package, the whole production line is forced to stop due to moisture absorption, thereby greatly reducing production ability of apparatus and greatly increasing product cost and production time and other hidden dangers.

Preparation methods for the injections of tigecycline crystalline hydrates are as follows:

Preparation method of freeze-dried powder injection formulation: the tigecycline crystalline hydrate, a pharmaceutically acceptable cosolvent, a pharmaceutically acceptable freeze-dried support agent or excipient, a stabilizer, water for injection are stirred for dissolving. Pharmaceutically acceptable acids or basics can be used to adjust the pH to the range of 4.0 to 7.5; then, 0.005 to 0.5% (W/V) of activated carbon are added to be stirred for 15 to 45 min, filtered, supplemented with water, and then sterilely filtered. The product is packed in a 25 to 100 mg/bottle (based on main drugs), freeze-dried, tamponaded, to give a finished product.

A pharmaceutically acceptable support agent or excipient can be one or several of glucose, lactose, xylitol, sorbitol, mannitol, dextran and the like, and these include anhydrous, aqueous or solvated carbohydrates, such as lactose including anhydrous lactose, lactose monohydrate, etc.

A pharmaceutically acceptable co-solvent may be a pharmaceutically acceptable inorganic acid or organic acid, an inorganic base or organic base, or it also can be a generalized Lewis acid or base which can include one or several Lewis acids or bases, and they can be one or several of hydrochloric acid, phosphoric acid, propionic acid, acetic acid, lactic acid, citric acid, tartaric acid, boric acid, polyhydroxy carboxylic acid such as glucuronic acid, gluconic acid, lactobionic acid, malic acid, threonic acid, glucoheptonic acid, 2,5-dihydroxybenzoic acid, acidic amino acids such as aspartic acid, glutamic acid, and the like.

A pharmaceutically acceptable pH adjusting agent may be a pharmaceutically acceptable inorganic or organic acid, an inorganic base or organic base, or it also can be generalized Lewis acid or an base, which may contain one or several selected from hydrochloric acid, phosphoric acid, propionic acid, acetic acid and acetates, such as sodium acetate, lactic acid and pharmaceutically acceptable salts thereof, pharmaceutically acceptable salts of citric acid, sodium carbonate, sodium hydrogen carbonate, potassium hydrogen carbonate, sodium hydroxide, potassium hydroxide, phosphate, tartaric acid and its pharmaceutically acceptable salt, borax, boric acid, succinic acid, caproic acid, adipic acid, fumaric acid, maleic acid, polyhydroxy carboxylic acid such as glucuronic acid, gluconic acid, lactobionic acid, malic acid, threonic acid, glucoheptonic acid, and pharmaceutically acceptable salts thereof.

A pharmaceutically acceptable antioxidant and stabilizer may be one or several of sulfurous acid, sulfite, bisulfite, pyrosulfite, dithionite, thiosulfate, an organic sulfur compound thiourea, glutathione dimercaprol, mercapto acetic acid and salts thereof, thiolactic acid and salts thereof, thiodipropionic acid and salts thereof, phenol compounds, such as gallic acid and salts thereof, caffeic acid or a pharmaceutically acceptable salt thereof, ferulic acid or pharmaceutically acceptable salts thereof, di-t-butyl phenol, 2,5-dihydroxy-benzoic acid or a salt thereof, salicylic acid or a salt thereof; ascorbic acid and ascorbates, isoascorbic acid and iso-ascorbate, nicotinamide, tartaric acid, nitrates, phosphate, pharmaceutically acceptable salt of acetic acid, citrate, EDTA and EDTA salts, such as EDTA disodium salt, EDTA tetrasodium, and the like.

Ways for removing heat sources and for sterilization may be as follows: removal of heat sources may be conducted by activated carbon in an amount of 0.005 to 3%, and sterilization can be conducted by means of microporous membrane and autoclaving. Ultra-filtration may be used to conduct the sterilization and removal of heat sources. An ultrafilter may be in a model selected from the group consisting of flat, roll, tubular, hollow fiber or round cassette, and preferably roll and hollow fiber shape. After most pyretic materials and bacteria are removed with a filter membrane which can retain substances having a relative molecular weight in the range of 50,000 to 300,000, residual heat sources are removed by using an ultra-filtration membrane which can retain substances having a relative molecular weight in the range of from 4,000 to 30,000, preferably a ultra-filtration membrane which can retain substances having a relative molecular weight in the range of from 6,000 to 30,000.

The preparation of the suppository of tigecycline crystalline hydrate may be as follow: The suppository consists of the tigecycline crystalline hydrates (generally, 1 to 40% by weight) and suppository matrix. The matrix may include one or several of ethanol, glycerol, glycogelatin, polyethylene glycol 200 to 8000, poloxamer, vaseline, semi-synthetic stearates (polyoxyl(40)stearate, propylene glycol stearate, fatty glycerides, etc.), the Carbomer series (931, 934, 940, 974, etc.), Tween 60-80, etc. Furthermore, the suppositories may comprise other pharmaceutically acceptable additives, such as stabilizers and absorption promoting agents. Preparation method: main drugs and matrix are mixed; the mixture is heated by a water bath with stirring, and after being melted, the mixture is stirred to be uniform; then, the uniform melt is rapidly poured into a suppository mold coated with a lubricant until it slightly overflows from suppository mold, and after cooling, the mold is flattened, drawn to get the product.

The tigecycline crystalline hydrates of the invention are suitable for applications in the manufacture of medicaments for treatment and prevention of infections of respiratory system, hepatobiliary system, facial features, urogenital, bone and joint infections, skin and soft tissue infections and mycoplasma and endocarditis, septicemia, meningitis and other diseases due to susceptible strains of Gram-positive or Gram-negative bacteria, anaerobic bacteria, Chlamydia in human or animal.

Dose and usage: under normal circumstances, the tigecycline crystalline hydrate, intramuscular injection: 0.05 g to 0.10 g once, 1-2 times per day; for children, dose reduction based on body weight; intravenous injection: time 0.05 g to 0.10 g once, 1-2 times per day; for children, dose reduction based on body weight, administered 1-2 times. Before use, the compound is diluted with sterile water for injection or sodium chloride injection in an appropriate amount. Administration manners of solid dosage are oral administrations or topical administrations, including vaginal delivery. Dose and usage of vaginal tablet and vaginal capsule: under normal circumstances, the usual dose for adults: 1-2 times per day, each time 0.05 g to 0.10 g; suppository usage: adult dose of 0.05 g to 0.10 g once, 1-2 times per day.

DESCRIPTION OF THE PREFERRED EMBODIMENTS

Unless indicated otherwise in Examples and other parts, all numbers used in the description and claims should be understood to be modified with the wording "about" in all the examples. Hence, unless otherwise indicated, number parameters given in the description and the claims attached should be approximations, which may be varied in accordance with properties sought by the present disclosure, and to say the least, it is not intended to limit the application of the principles of the scope of claims, each numerical parameter should be explained by considering the number of effective digits and conventional rounding methods.

Although numerical ranges ad parameters having a broad scope in the disclosures are set to be approximations, values given in specific examples are reported as precisely as possible. Any value essentially contains errors necessarily provided due to standard deviations found in their tests.

It should be noted that unless explicitly illustrated otherwise, the singular form of "a", "and" or "the" used in the present description and the claims attached therewith contains plural forms of corresponding references. Thus, for example, if a composition comprising "a compound" is mentioned, it means a mixture comprising two or more compounds. In addition, it should be noted that unless explicitly illustrated otherwise, the term "or" generally includes the expression "and/or".

As used herein, the term "obtained compound" refers to valuable compounds in a high purity level obtained from separation. The purity level includes, but not limited to, the purity level of greater than 90%, 95%, 96%, 97%, 98% and 99%. Said purity levels are measured by HPLC.

Pharmaceutical Compositions

The term "pharmaceutical composition" as used herein refers to a composition of drugs, and said pharmaceutical composition may comprise at least one pharmaceutically acceptable carrier.

The term "pharmaceutically acceptable excipient" as used herein refers to a pharmaceutical carrier or vehicle for the administration of compounds provided herein, including any carrier of the kind well known for a person skilled in the art which can be suitable for specific administration manners, for example, solutions or suspensions for parenteral, intradermal, subcutaneous or topical administrations can include sterile diluents (e.g., water for injection, saline solution, non-volatile oil and the like), synthetic fatty solvents (e.g., polyethylene glycol, glycerol, propylene glycol, etc.), antibacterial agents (e.g., benzyl alcohol, methylparaben, ethylparaben, etc.), antioxidants (e.g., ascorbic acid, sodium hydrogen sulfite, etc.), chelating agents (e.g., EDTA, etc.), buffers (phosphate, citrate, etc.), and/or substances for regulating the osmotic pressure (e.g., sodium chloride, glucose, etc.), or mixtures thereof. For further example, on intravenous administration, appropriate carriers include a physiological saline, a phosphate buffer and a solution containing thickeners, for example, glucose, polyethylene glycol, and mixtures thereof.

As a non-limiting example, the tigecycline may be optionally mixed with one or more pharmaceutically acceptable excipients, and can be orally administered in the following forms: tablets, capsules, dispersible powders, granules or suspensions containing, for example, about 0.05 to 5% of suspending agents, syrups containing, for example, about 10-50% of sucrose, and formulations containing, for example, about 20-50% of ethanol; or can be parenterally administered in a sterile solution form or a suspension form, wherein said suspension contains 0.05 to 5% of suspending agents in an isotonic medium. The pharmaceutical preparations may comprise, for example, about 25% to about 90% of active ingredients and carriers, and more usually, 5% to 60% (by weight) of active ingredients.

In order to further illustrate the present invention, preferred embodiments of the present invention are described in combination with following examples. However, it should be understood that these descriptions are only used for further illustration of features and advantages of the present invention, but not for limitation for the claims of the present invention.

Following examples are used to illustrate effects of the present invention, but the protection scope of the present invention is not limited by the following examples.

Thermal Analysis Method

Test conditions for the thermal analysis: Setaram Inc. Setsys 16, sample amount: from about 3 to about 10 mg, the rate for raising temperature: 10 K/min, $N_2$ flowing speed: 50 ml/min, temperature: from room temperature to about 400° C.

Surprising and characteristically, the thermograms (TG-DTA or TG-DSC) for the hydrates of the present invention have corresponding heat-absorption peaks under the weightlessness platform. The thermograms show tigecycline crystalline hydrates, such as tigecycline.$0.5H_2O$ hydrate, tigecycline.$2H_2O$ hydrate, tigecycline.$4H_2O$ hydrate and so on, and the same one crystalline hydrate may have a different crystalline form. Worthy to be pointed out, the TG profile of tigecycline.$2H_2O$ hydrate is characterized in that it shows a platform upon heating from 25° C. to 50° C., and there are no obvious weightlessness. However, obvious weightlessness is exhibited at the temperature in the range of 53° C. to 115° C., and Karl Fischer test proves that the weightlessness is due to water molecules.

Powder X-Ray Diffraction Method

The following conditions are used to determine powder X-ray diffraction patterns of tigecycline crystalline hydrates: D/MX-IIIA X-ray diffractometer, voltage: 35 kv, current: 30 mA, scanning speed: 10°/min, step size: 0.02°/step; copper target, monochromator: graphite monochromator; wavelength (Å): 1.54, diffraction angle: 2θ, the scanning range: 3-60°, all peak positions are in the range of ±0.2° 2θ.

In one embodiment, by using the powder X-ray diffraction method and in the measurement range of diffraction angle 2θ (3-60°), the tigecycline.$0.5H_2O$ hydrate of the present invention can have corresponding characteristic values at the following 2θ positions (FIG. 2): about 5.06, 8.2, 10.2, 11.0, 13.1, 13.5, 14.6, 15.4, 16.6, 17.6, 18.9, 19.2, 19.6, 21.0, 21.3, 22.3, 23.0, 24.6, 26, 26.4, 26.8, 27.4, 40.0, 40.2.

In another embodiment, by using the powder X-ray diffraction method and in the measurement range of diffraction angle 2θ(3-60°), the tigecycline.$2H_2O$ hydrate of the present invention can have corresponding feature values at the following 2θ positions (FIG. 4): about 5.03, 9.08, 10.06, 10.58, 11.56, 13.17, 14.38, 15.29, 17.55, 18.51, 19.67, 20.28, 21.31, 22.16, 22.79, 26.51, 29.31, 30.51, 33.92.

Test for Hygroscopicity

The tigecycline hydrates of the present invention may be stable for storage. Samples of tigecycline hydrates and anhydrides and amorphous tigecycline are used to conduct the test for hygroscopicity: respectively, about 5 g tigecycline anhydrides (obtained by drying tigecycline.$0.5H_2O$ hydrate prepared according to Example 1), about 5 g amorphous tigecycline (prepared by referring to the process as described in the reference document CN101367747A) and about 5 g the hydrates of the present invention are placed in a dry and constant weight watch glass, and the system is precisely weighed. At 25° C. and with the relative humidity of about 70%, hygroscopic weight-gaining percentages of the hygroscopicity test are calculated by sampling at 0 h and 12 h in the test, respectively, and the results show that the hygroscopicity of anhydrides is more higher than the hydrates of the present invention, and the tigecycline crystalline hydrates of the present invention may be stored more stably (shown in Table 1).

TABLE 1 results of hygroscopicity test

| The sampling time (12 hours) | As compared to the sample time of 0 h, weight gains % |
|---|---|
| Tigecycline•2 H$_2$O hydrate (prepared in Example 3) | 0.1% |
| Tigecycline•0.5 H$_2$O hydrate (prepared in Example 1) | 0.2% |
| Tigecycline anhydride | 1.4% |
| Amorphous tigecyline | 1.3% |

DESCRIPTION OF THE PREFERRED EMBODIMENTS

Example 1

Preparation of Tigecycline.0.5H$_2$O Hydrate

1) Preparation of 9-Nitro Minocycline

Minocycline hydrochloride (1, 100 g, 0.202 mol) is dissolved in 300 ml of a concentrated sulfuric acid which is pre-cooled to 0° C., and then under the temperature of −5° C. to 5° C., potassium nitrate (22.4 g, 0.24 mol) or fuming nitric acid (11.3 ml, 0.24 mol) are slowly added thereto. After the addition is completed, the mixture is continuously stirred for 1.5 hours at the temperature of from −5 to 5° C.; 2.4 L of a pre-cooled cyclohexane is slowly added, filtered, and washed with a small amount of ice cyclohexane, and the obtained solids are collected. The solids are dried under vacuum at 40 to 50° C. to give a yellow 9-nitro minocycline disulfate (2, 124.8 g, about 90%).

2) Preparation of 9-Amino Minocycline 9-nitro minocycline disulfate (2, 100 g, 0.143 mol) is added to a mixture of 2% palladium on carbon (40 g), 300 ml of 2N sulfuric acid solution and 400 ml of ethylene glycol monomethyl ether, and the obtained mixture is pressure hydrogenated for 1.5 hours. The catalyst is filtered off, and the obtained filtrate is added slowly to 3.5 L of isopropanol at 0 to 5° C., filtered to give yellowish crystals. The crystals are dried at 40° C. under vacuum to give 9-amino minocycline disulfate (3, 86.8 g, about 87%).

3) Preparation of Tigecycline

Figure 1:
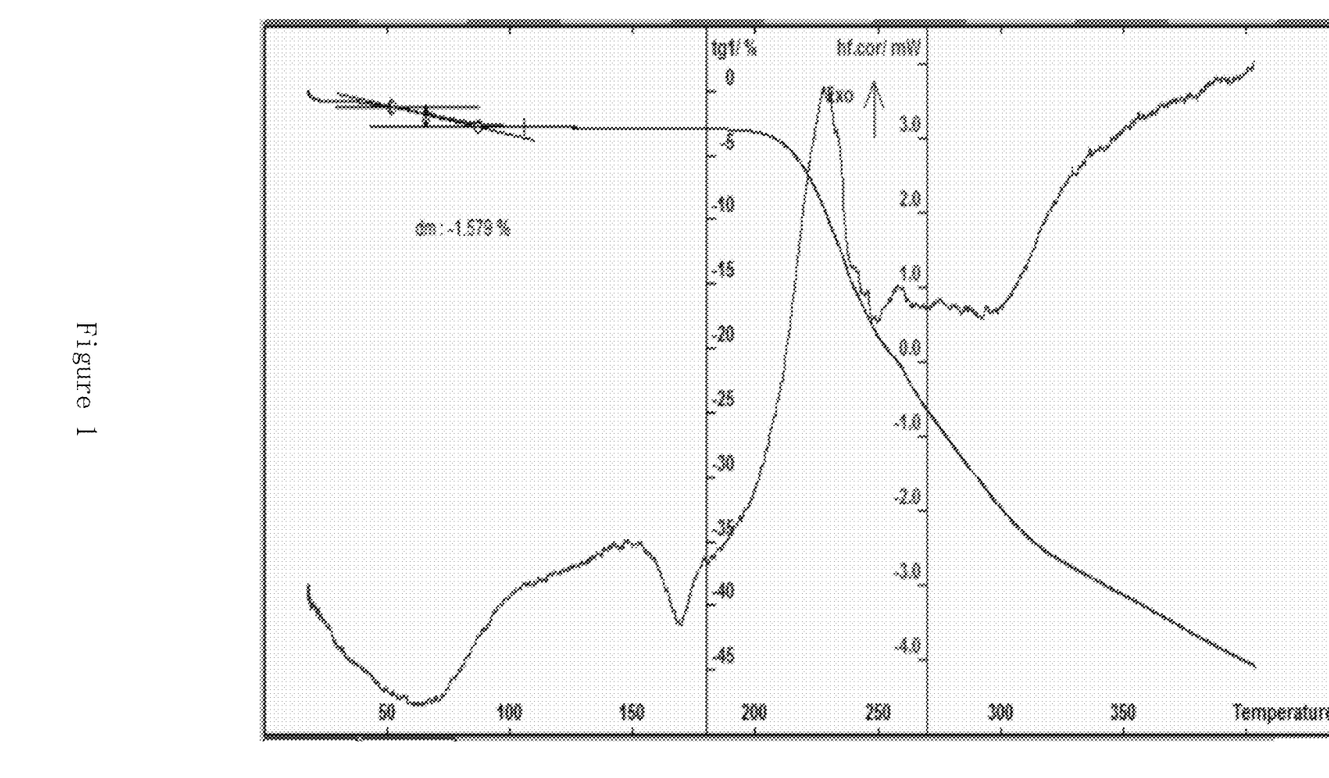
FIG. 1 shows a thermogram of a tigecycline.0.5H$_2$O hydrate (Example 1).
Figure 2:
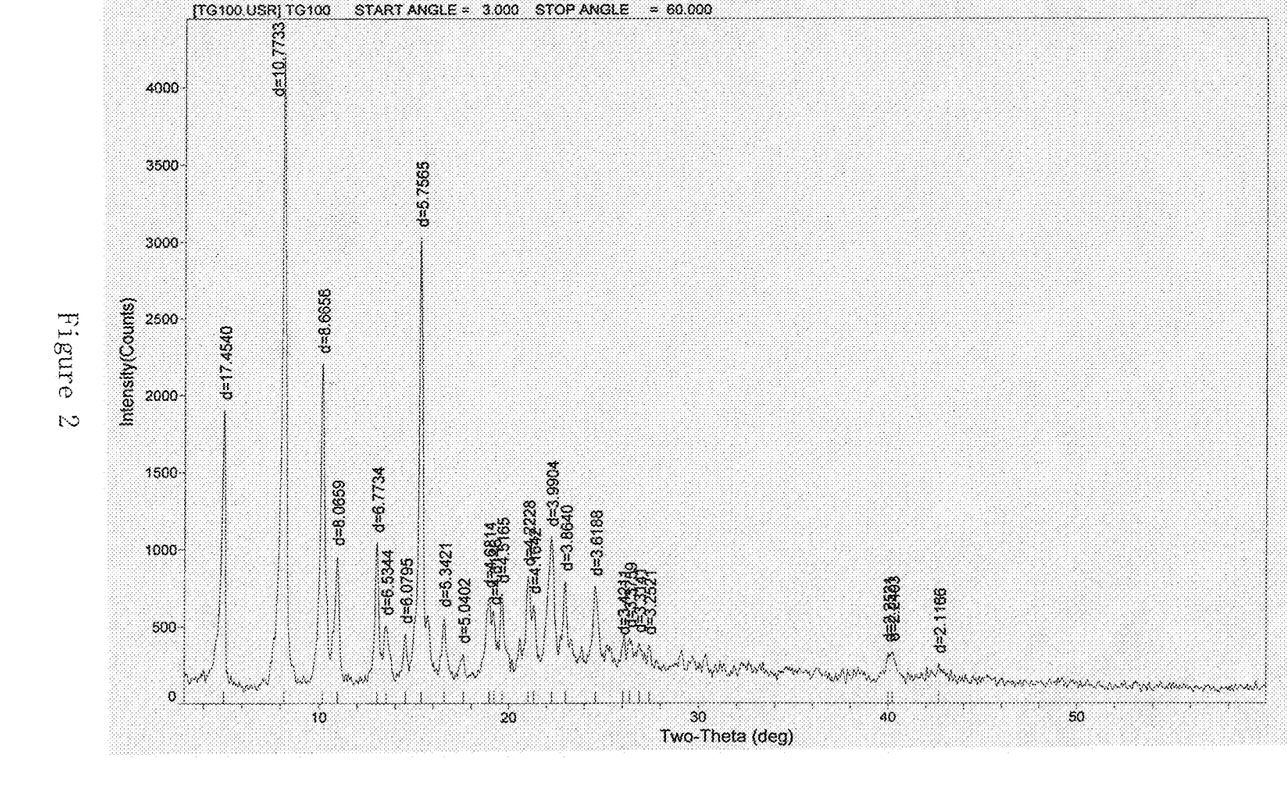
FIG. 2 shows a powder X-ray diffraction pattern of a tigecycline.0.5H$_2$O hydrate (Example 1).

Direct Acylation of 9-Amino Minocycline with N-Tert-Butyl Acetyl Chloride or N-Tert-Butyl Acetic Acid 9-amino minocycline disulfate (3, 20 g, 0.029 mol) and sodium carbonate (15 g) are suspended in a mixed solvent of 1,3-dimethyl propylene urea (400 ml) and acetonitrile (100 mL), and a solution of N-tert-butyl acetyl chloride (9.1 g, 0.058 mol) and 1,3-dimethyl propylene urea (600 ml)/acetonitrile (150 ml) is added dropwise with stirring at room temperature. The solution is continuously stirred for 30 min. After the completion of the reaction, 10 ml of methanol are added to terminate the reaction. The obtained reaction solution is poured into a mixed solution of isopropanol/diethyl ether, and a concentrated hydrochloric acid is added thereto, thereby resulting in crystallization. The mixture is filtered to give a yellow crystal which is tigecycline hydrochloride (5.HCl, 13.2 g, 0.021 mol, about 72%). Tigecycline hydrochloride is dissolved in deionized water, and 10% aqueous ammonia is added to adjust the pH to about 7.0, thereby an orange solid is precipitated. The solid is filtered, recrystallized with methane dichloride and water, and placed at 4° C. for 8 hours, and after this, the system is suction filtered. The obtained solid is dried at 40° C. under vacuum for 2 h to give a tigecycline hydrate (9.6 g); MS (FAB): m/z: 586 (M+H), 585.5 (M$^+$); moisture measured by the Cartesian method: 1.79%, the thermal analysis: about 1.58% of platform weightlessness (FIG. 1). These results and the results of the sample comprising 0.5 crystalline water are within the error range; X powder diffraction pattern shows obvious characteristic peaks (FIG. 2); IR spectrum: $v^{KBr}_{max}$ cm$^{-1}$ 3440, 3312, 3197, 2968, 2936, 2871, 2871, 2792, 2724, 1641, 1614, 1531, 1390, 1367, 1282, 1242, 1205, 1179, 1105, 1057, 1024, 998, 971, 873, 805, 704; Elemental analysis calcd: C, 58.57%; H, 6.78%; N, 11.78%. Found: C, 58.66%; H, 6.89%; N, 11.89%.

A small quantity of the solid product in the example is dried under vacuum at about 60° C. in the presence of phosphorus pentoxide for 24 h, and after cooling, the system is placed for 12 h to give the corresponding anhydride.

Example 2

Preparation of Tigecycline.2H$_2$O Hydrate

Figure 3:
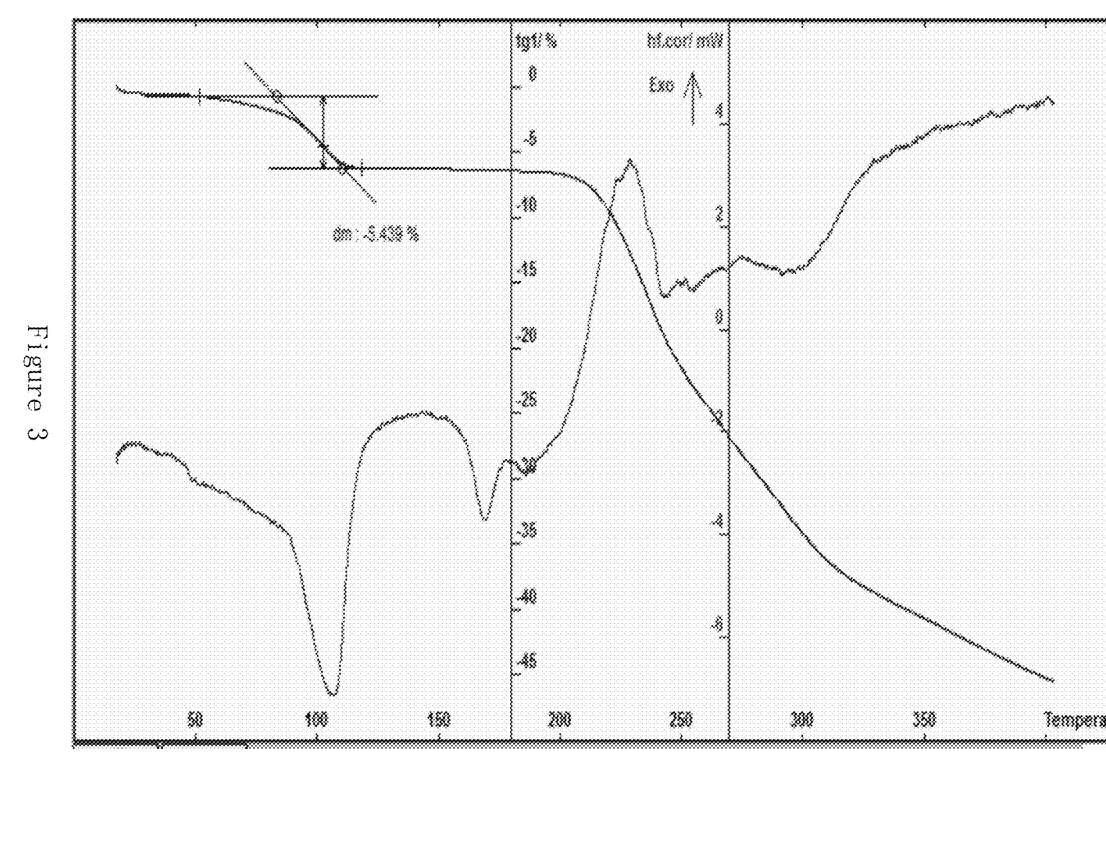
FIG. 3 shows a thermogram of a tigecycline.2H$_2$O hydrate (Example 2).
Figure 4:
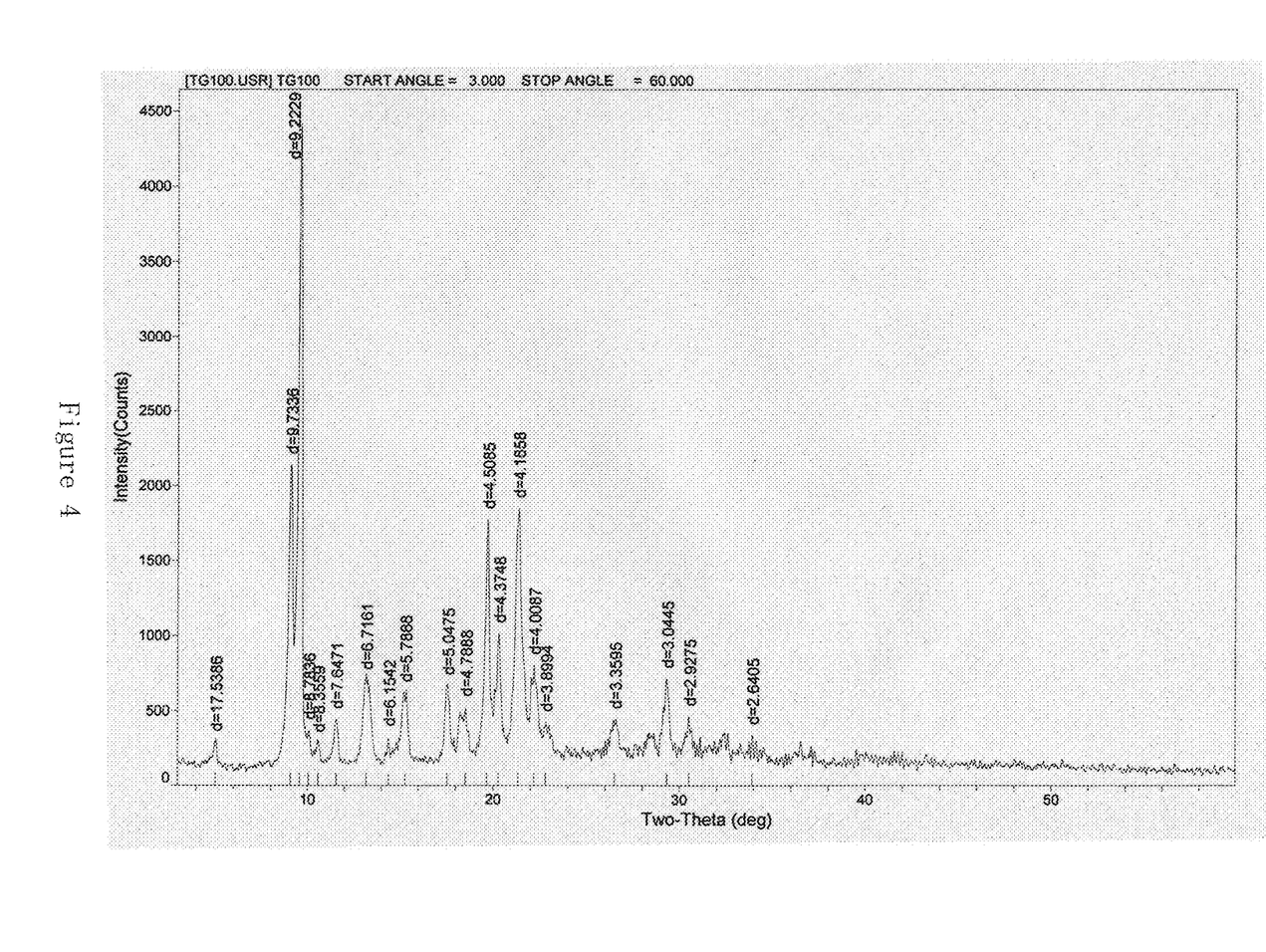
FIG. 4 shows a powder X-ray diffraction pattern of a tigecycline.2H$_2$O hydrate (Example 2).

In a reaction flask, 9-bromoacetylamino minocycline hydrobromide (15 g, 0.022 mol), tert-butylamine (11.6 ml, 0.11 mol) and 100 ml of methanol are mixed together, and stirred at room temperature for 30 min. The mixture is filtered to remove precipitations; the obtained filtrate is concentrated under reduced pressure; the residue is recrystallized with methanol, methane dichloride, and water, left still for about 8 hours at 4° C., and filtered, and the obtained solids are dried under vacuum at 40° C. for 2 hours to give red-orange crystals, tigecycline.2H$_2$O hydrate (9.3 g); ESI-MS: m/z: 585.5 (M); moisture content measured by the Cartesian method: 5.96%, thermal analysis: about 5.44% of platform weightlessness (FIG. 3). These results and the results of the sample comprising 2 crystalline water are within the error range (theoretical value of 5.80%); X powder diffraction pattern shows obvious characteristic peaks (FIG. 4); Elemental analysis: calcd: C, 56.03%; H, 6.97%; N, 11.27%. Found: C, 55.91%; H, 6.79%; N, 11.34%.

Example 3

Preparation of Tigecycline.4H$_2$O Hydrate

Figure 5:
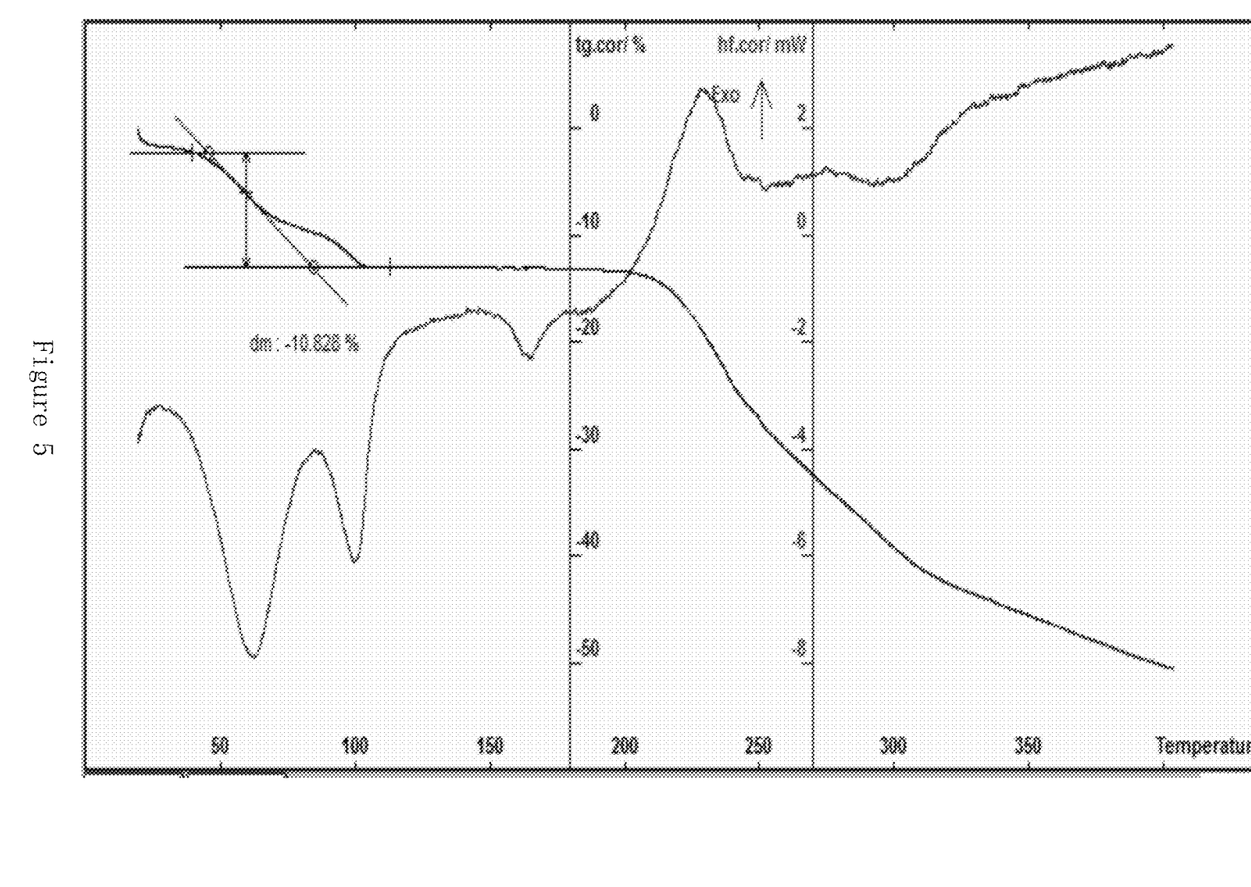
FIG. 5 shows is a thermogram of a tigecycline.4H$_2$O hydrate (in Example 3).

In a reaction flask, 9-chloroacetylamino minocycline hydrochloride (10 g, 12.9 g, 0.022 mol), tert-butylamine (11.6 ml, 0.11 mol) and 100 ml of methanol are mixed together, and stirred at room temperature for 30 min. The mixture is filtered to remove precipitations; the obtained filtrate is concentrated under reduced pressure; the residue is crystallized with methanol and water, and then further recrystallized with methanol and water; the crystalline system is left overnight at 4° C., suction filtered to give solids, and the solids are dried under vacuum at 40° C. for 2 hours to give red-orange crystals, tigecycline.4H$_2$O hydrate (8.3 g); MS (FAB): m/z: 586.5 (M+H), 585.5 (M$^+$); moisture content measured by the Cartesian method: 11.34%, thermal analysis: about 10.83% of platform weightlessness (FIG. 5). These results and the results of the sample comprising 4 crystalline water are within the error range (theoretical value 10.96%); X powder diffraction pattern shows obvious characteristic peaks; Elemental Analysis Calcd: C, 52.96%; H, 7.20%; N, 10.65%. Found: C, 52.90%; H, 7.34%; N, 10.57%.

Example 4

Preparation of the Lyophilized Formulation

A tigecycline hydrate (10 g) (prepared according to Example 1 or Example 2 or Example 3 or Example 4) is taken, and 1N hydrochloric acid is added thereto to make the hydrate dissolved. Then, mannitol (10 g) and disodium EDTA (0.05 g) are added to the solution, and then about 160 to 220 ml of water for injection saturated with nitrogen gas are added to make them dissolved with stirring. The pH is adjusted to be 5.5 to 7.0 with an about 1M solution of phosphoric acid and sodium dihydrogen phosphate, and 0.01 to 0.5% (W/V) of activate carbon are added thereto. The mixture is stirred for 15 to 30 min, filtered with 0.22 micron micro-porous membrane. The product is packed in the form of 0.05 g/bottle or 0.1 g/bottle, freeze-dried under vacuum, tamponaded, to get the finished products.

Example 5

Preparation of the Lyophilized Formulation

A tigecycline hydrate (10 g) (prepared according to Example 1 or Example 2 or Example 3 or Example 4) is taken, and 1N hydrochloric acid is added thereto to make the hydrate dissolved. Then, lactose (10 g) and disodium EDTA (0.05 g) are added to the solution, and then about 160 to 220 ml of water for injection saturated with nitrogen gas are added to make them dissolved with stirring. The pH is adjusted to be 4.5 to 7.0 with an about 1M solution of phosphoric acid and sodium dihydrogen phosphate, and 0.01 to 0.5% (W/V) of activate carbon are added thereto. The mixture is stirred for 15 to 30 min, filtered with 0.22 micron microporous membrane. The product is packed in the form of 0.05 g/bottle or 0.1 g/bottle, freeze-dried under vacuum, tamponaded, to get the finished products.

Example 6

Buccal Tablets of Tigecycline Crystalline Hydrates (50 Mg/Tablet)

Formulation:
Tigecycline hydrates 50 g
Instant sorbitol 320 g
Microcrystalline cellulose 20 g
Low-substituted hydroxypropyl cellulose 10 g
Magnesium stearate 2 g
A Tigecycline crystalline hydrate (prepared according to Example 1 or Example 2 or Example 3 or Example 4), instant sorbitol, microcrystalline cellulose, low-substituted hydroxypropyl cellulose, magnesium stearate are passed through a 100 mesh sieve, mixed uniformly, and then pressed into a large tablet; subsequently, the large tablet is grinded into 18 to 24 mesh granules, then compressed into tablets.

Example 7

Tigecycline.2H$_2$O Hydrate Tablets (50 Mg/Tablet)

Formulation:
Tigecycline hydrates 50 g
Instant sorbitol 320 g
Microcrystalline cellulose 20 g
Low-substituted hydroxypropyl cellulose 10 g
Magnesium stearate 2 g
A tigecycline crystalline hydrate (prepared according to Example 1 or Example 2 or Example 3 or Example 4), instant sorbitol, microcrystalline cellulose, low-substituted hydroxypropyl cellulose, magnesium stearate are passed through a 100 mesh sieve, mixed uniformly, and then pressed into a large tablet. Subsequently, the large tablet is grinded into 18 to 24 mesh granules, then compressed into tablets.

Example 8

Tigecycline.0.5H$_2$O Hydrate Tablets (100 Mg/Tablet)

Formulation:
Tigecycline.0.5H$_2$O hydrates 100 g
Mannitol 185 g
Low-substituted hydroxypropyl cellulose 45 g
5% PVP K-30 (50% ethanol aqueous solution) suitable amounts
Magnesium stearate 4 g
A tigecycline.0.5H$_2$O hydrate (prepared according to Example 1), mannitol, and low-substituted hydroxypropyl cellulose are passed through a 100 mesh sieve, and mixed uniformly. A suitable amount of 5% PVP K30 in 50% ethanol aqueous solution is used as adhesive for making a soft material. The obtained product is passed through a 18 to 24 mesh sieve to get granules, dried, and then the granules are through a 14 to 20 mesh sieve; after this, magnesium stearate is added to mix, then compressed into tablets.

Example 9

Preparation Of Tigecycline Hydrate Capsules of the Present Invention (Main Drug 50 Mg/Granule)

Formulation:
Tigecycline hydrate, 50 g
Cysteine hydrochloride 2 g
A tigecycline.0.5H$_2$O hydrate (prepared according to Example 1 or Example 2 or Example 3 or Example 4) and cysteine hydrochloride are through a 100 mesh sieve, respectively, mixed uniformly, and then they are prepared into capsules.

Example 10

Preparation of Tigecycline Hydrate Capsules of the Present Invention (Main Drug 100 Mg/Granule)

Formulation:
Tigecycline hydrate, 100 g
Cysteine hydrochloride 4 g
A tigecycline.2H$_2$O hydrate (prepared according to Example 3 or Example 4) and cysteine hydrochloride are through a 100 mesh sieve, respectively, mixed uniformly, and then they are prepared into capsules.

Example 11

Suppository of Tigecycline Crystalline Hydrates (50 Mg/Granule)

Formulation:
Tigecycline crystalline hydrate 5 g (100 granule feeding)

Polyethylene glycol 4000 110 g
Polyethylene glycol 1500 60 g
Glycerol 5 ml
Poloxamer 30 g
Disodium EDTA 1 g A tigecycline crystalline hydrate (prepared according to Example 1 or Example 2 or Example 3 or Example 4), glycerol, polyethylene glycol 1500, polyethylene glycol 4000, poloxamer, and EDTA disodium are mixed, heated in a water bath, and stirred, and after the mixture is melted, the melt is stirred to be uniform. Then, it is rapidly poured into a suppository mold coated with a lubricant to slightly overflow suppository mold, and after cooling, the mold is flatten, drawn to obtain the product.

It can be understood that from professional view, variations of many details are possible, but this cannot limit the scope and spirit of the present invention. Hence, the present invention is not limited to the above embodiments.

The invention claimed is:

1. A tigecycline crystalline hydrate, the tigecycline crystalline hydrate having a molecular formula of $C_{29}H_{39}N_5O_8 \cdot nH_2O$, where n=0.5, 2 or 4.

2. A method for the preparation of the tigecycline crystalline hydrate according to claim 1, wherein the method is selected from the group consisting of:
method A comprising direct acylation of 9-aminominocycline with N-tert-butyl acetyl chloride or N-tert-butyl acetic acid comprising:
  suspending 9-amino minocycline disulfate, and sodium hydrogen carbonate or sodium carbonate or potassium carbonate in a mixed solvent of 1,3-dimethyl propylidene urea/a lower $C_2$-$C_6$ nitrile;
  adding a solution of N-tertbutyl acetyl chloride and 1,3-dimethyl propylidene urea/a lower $C_2$-$C_6$ nitrile at room temperature with stirring to form a mixture;
  after the addition, stirring the mixture continuously for about 0.3-2h;
  adding a low-molecular $C_1$-$C_6$ alcohol to terminate the reaction;
  pouring the mixture into one or more solutions selected from the group consisting of a low-molecular $C_1$-$C_6$ alcohol, lower $C_2$-$C_6$ nitrile, and a lower $C_2$-$C_8$ ether, and adding a concentrated hydrochloric acid thereto to precipitate a first set of tigecycline hydrochloride crystals; filtering out the first set of tigecycline hydrochloride crystals;
  dissolving the first set of tigecycline hydrochloride crystals in deionic water, and adding aqueous ammonia to adjust the pH to about 6.8-7.8, to precipitate a second set of tigecycline hydrochloride crystals;
  filtering out the second set of tigecycline hydrochloride crystals and recrystallizing the obtained tigecycline hydrochloride crystals one or more times with water and a solvent selected from the group consisting of a low substituted halogenated $C_1$-$C_6$ hydrocarbon, a lower $C_3$-$C_8$ ketone, a low-molecular $C_1$-$C_6$ alcohol, a lower $C_2$-$C_6$ nitrile, a lower $C_2$-$C_8$ ester, a lower $C_2$-$C_8$ ether, and a $C_6$-$C_{12}$ aromatic hydrocarbon; and
  drying the obtained tigecycline hydrochloride crystals to give the tigecycline crystalline hydrate; or
method B comprising amination of 9-haloacetylamino minocycline with tert-butylamines comprising:
  mixing 9-bromoacetylamino minocycline hydrobromide or 9-chloroacetylamino minocycline hydrochloride with tert-butyl amine and a low-molecular $C_1$-$C_6$ alcohol to form a mixture,
  stirring the mixture at room temperature for about 0.3-2 h, and filtering to remove precipitation, forming a filtrate;
  concentrating the filtrate under reduced pressure;
  recrystallizing the residual one or more times with water and a solvent selected from the group consisting of a low substituted halogenated $C_1$-$C_6$ hydrocarbon, a lower $C_3$-$C_8$ ketone, a low-molecular $C_1$-$C_6$ alcohol, a lower $C_2$-$C_6$ nitrile, a lower $C_2$-$C_8$ ester, a lower $C_2$-$C_8$ ether, and a $C_6$-$C_{12}$ aromatic hydrocarbon, and
  filtering to give a tigecycline crystalline hydrate;
  wherein the weight-volume ratios of 9-bromoacetylamino minocycline hydrobromide or 9-chloroacetylamino minocycline hydrochloride (g): tert-butylamine (ml): a low-molecular $C_1$-$C_6$ alcohol (ml) [[=]] are about 10-15: 10-20: 100-200.

3. A pharmaceutical composition comprising pharmaceutically acceptable salts of the tigecycline crystalline hydrate according to claim 1.

4. A pharmaceutical composition comprising the tigecycline crystalline hydrate according to claim 1.

5. A pharmaceutical composition comprising the tigecycline crystalline hydrate according to claim 1, wherein the composition is selected from the group consisting of a solid preparation, an injectable preparation, and a suppository.

6. A method of treating or preventing a disease or condition comprising administering to an individual in need thereof a therapeutically or prophylactically effective amount of the tigecycline crystalline hydrate according to claim 1, wherein the disease or condition is selected from the group consisting of infection of respiratory system, hepatobiliary system, facial features, urogenital system, bone, joint, skin and soft tissue, and endocarditis, septicemia, meningitis caused by susceptible strains of Gram-positive or-negative bacteria, anaerobic bacteria, chlamydia, and mycoplasma in human or animal.

7. The method according to claim 2, wherein the recrystallization solvent for the tigecycline crystalline hydrates is selected from the group consisting of water, acetonitrile, acetone, tetrahydrofuran, methanol, ethanol, isopropanol, ethyl acetate, dichloromethane, chloroform, diethyl ether, diisopropyl ether, and benzene.

8. The tigecyline crystalline hydrate according to claim 1, wherein the tigecycline.0.5 H2O hydrate has corresponding characteristic values at the following 2θ positions at diffraction angle 2θ (3-60°) in the powder X-ray diffraction patterns: 5.06, 8.2, 10.2, 11.0, 13.1, 13.5, 14.6, 15.4, 16.6, 17.6, 18.9, 19.2, 19.6, 21.0, 21.3, 22.3, 23.0, 24.6, 26, 26.4, 26.8, 27.4, 40.0, 40.2, all peak positions are in the range of ±0.2° 2θ.

9. The tigecyline crystalline hydrate according to claim 1, wherein the tigecycline.2 H2O hydrate has corresponding characteristic values at the following 2θ positions at diffraction angle 2θ (3-60°) in the powder X-ray diffraction patterns: 5.03, 9.08, 10.06, 10.58, 11.56, 13.17, 14.38, 15.29, 17.55, 18.51, 19.67, 20.28, 21.31, 22.16, 22.79, 26.51, 29.31, 30.51, 33.92, all peak positions are in the range of ±0.2° 2θ.

10. The method of claim 2, wherein the method is method A.

11. The method of claim 2, wherein the method is method B.

12. The pharmaceutical composition of claim 5, wherein the composition is a solid preparation and the solid preparation is selected from the group consisting of tablets, capsules, and granules.

13. The pharmaceutical composition of claim 5, wherein the composition is an injectable preparation and the injectable preparation is a freeze-dried powder.

* * * * *